United States Patent [19]

Alt et al.

[11] 4,288,242

[45] Sep. 8, 1981

[54] ALPHA-CHLORO-ALKOXYMETHYL-N-(2,6-DIALKOXYPHENYL)ACETAMIDES AS EFFECTIVE TURFGRASS REGULANTS

[75] Inventors: Gerhard H. Alt, University City; John P. Chupp, Kirkwood, both of Mo.

[73] Assignee: Monsanto Company, St. Louis, Mo.

[21] Appl. No.: 133,762

[22] Filed: Mar. 25, 1980

[51] Int. Cl.$^3$ ............................................. A01N 37/24
[52] U.S. Cl. .......................................... 71/76; 71/118
[58] Field of Search ...................................... 71/118, 76

[56] References Cited

U.S. PATENT DOCUMENTS

| | | | |
|---|---|---|---|
| 3,442,945 | 5/1969 | Olin | 71/118 X |
| 3,475,155 | 10/1969 | Ishida et al. | 71/118 |
| 3,547,620 | 12/1970 | Olin | 71/118 |

Primary Examiner—Catherine L. Mills
Attorney, Agent, or Firm—William I. Andress; Donald W. Peterson

[57] ABSTRACT

This disclosure relates to a class of alpha-chloro-N-alkoxymethyl-N-(2,6-dialkoxyphenyl)acetamides which are effective in regulating the natural growth or development of plants. As employed herein, the term "natural growth or development" designates the normal life cycle of the plant in accordance with its genetics and its environment, in the absence of artificial, external influences. More particularly, this disclosure is concerned with a method wherein turfgrasses are treated with an alpha-chloro-N-alkoxymethyl-N-(2,6-dialkoxyphenyl)acetamide which serves to retard or reduce the rate of turfgrass growth. Such a treatment may also serve to retard or reduce the formation of seedheads and seedhead stalk elongation.

9 Claims, No Drawings

ALPHA-CHLORO-ALKOXYMETHYL-N-(2,6-DIALKOXYPHENYL)ACETAMIDES AS EFFECTIVE TURFGRASS REGULANTS

This invention relates to a class of alphachloro-N-alkoxymethyl-N-(2,6-dialkoxyphenyl)acetamides which are effective in regulating the natural growth or development of plants. As employed herein, the term "natural growth or development" designates the normal life cycle of the plant in accordance with its genetics and its environment, in the absence of artificial, external influences. More particularly, this invention is concerned with a method wherein turfgrasses are treated with an alpha-chloro-N-alkoxymethyl-N-(2,6-dialkoxyphenyl)acetamide which serves to retard or reduce the rate of turfgrass growth. Such a treatment may also serve to retard or reduce the formation of seedheads and seedhead stalk elongation.

It should be understood, however, that the regulation of natural growth or development discussed herein does not include herbicidal or killing action, and that the turfgrasses treated in accordance herewith are not unwanted plants.

Although lethal amounts of an alpha-chloro-N-alkoxymethyl-N-(2,6-dialkoxyphenyl)acetamide disclosed herein might be employed to obtain destruction or total inhibition of certain plants, it is contemplated here to employ only such amounts of said alpha-chloro-N-alkoxymethyl-N-(2,6-dialkoxyphenyl)acetamide as will serve to effectively regulate the natural growth or development of turfgrasses in the desired manner. As long understood and well recognized by those skilled in the art, such effective plant regulating amounts will vary, not only with the particular alpha-chloro-N-alkoxymethyl-N-(2,6-dialkoxyphenyl)acetamide selected for treatment, but also with the regulatory effect to be achieved, the species of plant being treated and its stage of development, and whether a permanent or transient regulating effect is sought. Other factors which may bear upon the determination of an effective plant regulating amount include the plant growth medium, the manner in which the treatment is to be applied, and weather conditions such as temperature and rainfall.

The term "turfgrass" is generally considered as encompassing a variety of specialized grasses which are employed in the development and/or management of certain areas for specific purposes, such as utility, beautification and recreation. Examples of such "turfgrasses" include Tall fescue, Red fescue, Kentucky bluegrass, Bermuda grass, Bahia grass, St. Augustine grass and the like. The use of a chemical treatment to reduce or retard the natural growth or development of turfgrass provides many advantages. Among the areas in which turfgrasses are most frequently used are roadbanks and medians which parallel long stretches of our highway system, the large grassy areas of golf courses and parks, the grounds which surround large educational or industrial institutions and, of course, the lawn of the homeowner. In all of such areas, it is readily apparent that a chemical treatment which serves to reduce or retard the rate of grass growth is highly desirable since it will serve to minimize the time and costs expended on maintenance. Such a treatment will also provide enhanced appearance by promoting grass height uniformity and by suppressing unsightly seedhead development.

In accordance with this invention, the desired retardation or reduction of the rate of growth of turfgrass is achieved by applying to turfgrass an effective amount of a compound of the formula

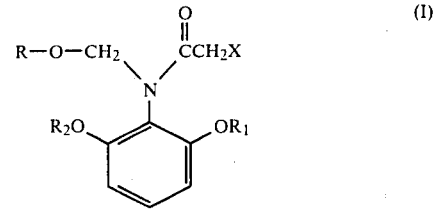

wherein R, $R_1$ and $R_2$ are independently lower alkyl and X is chloro, bromo or iodo.

As employed herein, the term "lower alkyl" designates alkyl radicals which have up to four carbon atoms in a straight or branched chain, such as, for example, methyl, ethyl, propyl, isopropyl, butyl, isobutyl, sec-butyl and t-butyl.

In accordance with the present invention, the compounds of formula (I) may be prepared utilizing a transetherification procedure as follows:

A compound of the formula

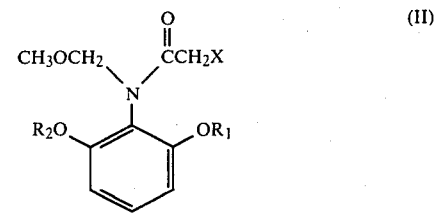

wherein X, $R_1$ and $R_2$ are above defined is reacted with a compound of the formula

wherein R is lower alkyl; in a solvent in the presence of an acid catalyst within a temperature range of 20° C. to 200° C.

It is preferred that the solvent employed in the process of the present invention be a compound of formula (III). Other suitable solvents which may be employed include aliphatic and aromatic hydrocarbons or halogenated hydrocarbons such as naphtha, the halogenated alkanes, e.g., carbon tetrachloride, chloroform, ethylene dichloride, trichloroethane, etc., benzene, halogenated benzenes, toluene, the xylenes and the like.

The temperature at which the process of this invention is conducted is not critical. The temperature should be one which is sufficiently elevated so as to initiate and maintain the reaction. It is preferred to employ temperatures in the range of from 25° C. to 100° C. Generally the temperature employed is the reflux temperature of the solvent employed.

Acid catalysts which may be used in the process of this invention include inorganic acids such as $H_2SO_4$, $H_3PO_4$; the hydrohalides, HCl, HBr, HI; sulfonic acids such as sulphamic acid, methane sulfonic acid, benzenesulfonic acid, p-toluenesulfonic acid, etc.; Lewis Acids, e.g., $BF_3$, $BF_3$ etherates, $AlCl_3$, etc. Other catalysts which can be employed within the process of this invention are salts of organic acids as acidic catalysts. Examples of such salts are the halides and acetates, oxalates, etc., of boron, copper and mercury. Also, acidic ion-exchange resins such as sulphonated styrene polymers or co-polymers which may contain from 1–15% by weight of a cross-linking agent such as divinylbenzene can be employed in the process of the present invention as an acid catalyst.

For ease of reaction and recovery of the reaction products, one can employ a molecular sieve. Molecular sieves which may be used herein include natural zeolites (alumino-silicates) or synthetic zeolites such as alkali metal alumino-silicate hydrates exemplified by Type 3A, i.e., $K_9Na_3 [(AlO_2)_{12} (SiO_2)_{12}].27H_2O$; Type 4A, i.e., $Na_{12} [(AlO_2)_{12} (SiO_2)_{12}].27H_2O$; Type 5A, i.e., $Ca_{4.5}Na_3 [(AlO_2)_{12}].3 H_2O$, etc. The criteria for selection of a particular molecular sieve is that its intercellular pore size be small enough to trap or absorb by-product alcohol while excluding larger molecules. As used herein, molecular sieves are preferably used to absorb methanol and water in embodiments in which these by-products are formed.

The following illustrative, non-limiting examples will serve to further demonstrate to those skilled in the art the manner in which specific compounds within the scope of this invention can be prepared. In the examples, all parts are parts by weight unless otherwise expressly stated.

EXAMPLE 1

A mixture containing alpha-chloro-N-[methoxymethyl]-N-[2,6-dimethoxyphenyl]acetamide (4.9 g; 0.018 mole), isopropanol (1.08 g; 0.018 mole) and 0.2 ml. of methane sulfonic acid in 150 ml. of xylene was heated at reflux temperature under a soxhlet extractor containing 20 g. of activated 3-A molecular sieves for 2 hours. The reaction mixture was then cooled to 26° C. after which time a 2.5% sodium chloride solution was added to the reaction mixture. The layers were separated and the organic layer was dried over magnesium sulfate, filtered and concentrated in vacuo to yield a semi-solid residue. The semi-solid residue was recrystallized from an ether-hexane mixture to yield alpha-chloro-N-[1-methylethoxymethyl]-N-[2,6-dimethoxyphenyl]acetamide (2.5 g; 46% yield) as a white solid having a melting point of 85°–90° C. and the following analysis:

Calculated: C, 55.72; H, 6.68; N, 4.64. Found: C, 55.79; H, 6.68; N, 4.67.

EXAMPLE 2

A mixture containing alpha-chloro-N-[methoxymethyl]-N-[2,6-dimethoxyphenyl]acetamide (4.0 g; 0.015 mole), 150 ml. of n-butanol and 0.2 ml. of methylsulfonic acid in 150 ml. of toluene was refluxed for 7 hours in a soxhlet extractor containing 22 g. of activated 3A molecular sieves. The reaction mixture was allowed to cool to 26° C. and was then washed with a 5% sodium carbonate solution. The organic layer was separated, dried over magnesium sulfate, filtered and concentrated in vacuo to yield a dark oil. The dark oil was distilled at 170° C. (0.05 mm) to yield alpha-chloro-N-(butoxymethyl)-N-(2,6-dimethoxyphenyl)acetamide (2.7 g; 57% yield) as a clear colorless oil having a boiling point of 170° C. at 0.05 mmHg and the following analysis:

Calculated: C, 57.05; H, 7.02; N, 4.44. Found: C, 57.03; H, 7.02; N, 4.47.

EXAMPLE 3

A mixture containing alpha-chloro-N-[methoxymethyl]-N-[2,6-dimethoxyphenyl]acetamide (4.4 g; 0.0161 mole), 150 ml. of n-propanol and 0.2 ml. of methanesulfonic acid was heated at reflux temperature for 9 hours in a soxhlet extractor containing 22 g. of activated 3A molecular sieves. The reaction mixture was allowed to stand at 26° C. for 16 hours and was then concentrated in vacuo yielding a crude product. The crude product was taken up in ether and the ether solution was washed with a 5% sodium carbonate solution. The layers were separated and the organic ether layer was dried over magnesium sulfate, filtered and concentrated in vacuo to yield a white solid. The white solid was recrystallized from hexane to yield alpha-chloro-N-[propoxymethyl]-N-[2,6-dimethoxyphenyl]acetamide (3.3 g; 68% yield) as a white solid having a melting point of 83°–85° C. and the following analysis:

Calculated: C, 55.72; H, 6.68; N, 4.64. Found: C, 55.65; H, 6.70; N, 4.62.

EXAMPLE 4

A mixture containing alpha-chloro-N-[methoxymethyl]-N-[2,6-dimethoxyphenyl]acetamide (4.9 g; 0.018 mole), 20 ml. of isobutanol and 0.2 ml. of methanesulfonic acid in 150 ml. of xylene was heated at reflux temperature for 2 hours under a soxhlet extractor containing 20 g. of activated 3A molecular sieves. The reaction mixture was then cooled to 26° C. after which time a 2.5% sodium chloride solution was added to the reaction mixture. The layers were separated and the organic layer was dried, filtered and concentrated to yield a yellow solid. The yellow solid was recrystallized from heptane to yield alpha-chloro-N-[2-methylpropoxymethyl]-N-[2,6-dimethoxyphenyl]acetamide (5.0 g; 88% yield) as white crystals having a melting point of 107°–110° C. and the following analysis:

Calculated: C, 57.05; H, 7.02; N, 4.44. Found: C, 57.11; H, 7.06; N, 4.44.

EXAMPLE 5

To a mixture containing alpha-chloro-N-(2,6-dimethoxyphenyl)acetamide (11.0 g; 0.048 mole), 10 ml. of (chloromethyl)methyl ether and 3.0 g. of benzyltriethylammonium bromide in 100 ml. of methylene chloride was added 50 ml. of a 50% sodium hydroxide solution. The temperature of the reaction mixture increased to 40° C. The reaction mixture was stirred for 1 hour after which time the layers were separated, and the organic methylene chloride layer was concentrated in vacuo yielding a white solid. The white solid was recrystallized from isopropanol to yield alpha-chloro-N-(methoxymethyl)-N-(2,6-dimethoxyphenyl)acetamide (11.8 g; 90% yield) as a white solid having a melting point of 104°–106° C. and the following analysis:

Calculated: C, 52.66; H, 5.89; N, 5.12. Found: C, 52.58; H, 5.99; N, 5.10.

EXAMPLE 6

To a mixture containing potassium hydride (2.2 g; 0.055 mole) in 50 ml. of tetrahydrofuran was added a solution of alpha-chloro-N-(2,6-dimethoxyphenyl)acetamide (11.5 g; 0.05 mole) in 250 ml. of tetrahydrofuran. Hydrogen gas evolved from the reaction mixture. To the reaction mixture was added an excess of (chloromethyl)ethyl ether (10 ml.) which caused the temperature of the reaction mixture to increase to 45° C. An excess of a sodium bicarbonate solution (100 ml.) was then added to the reaction mixture followed by the addition of 100 ml. of diethyl ether. The layers were separated and the organic ether layer was dried over magnesium sulfate, filtered and concentrated in vacuo to yield an amber oil. The amber oil was separated on a silica gel column using a 3:2 hexane:diethyl ether mixture as the eluant. Fractions containing a crude product were combined and concentrated in vacuo to yield a solid residue. The solid residue was taken up in pentane and the pentane solution was scratched until a white solid formed. The pentane solution containing the white solid was filtered and the white solid was recrystallized from heptane to yield alpha-chloro-N-(ethoxymethyl)-N-(2,6-dimethoxyphenyl)acetamide (3.0 g; 20.9% yield) having a melting point of 95°–97° C. and the following analysis:

Calculated: C, 54.26; H, 6.31; N, 4.87. Found: C, 54.22; H, 6.34; N, 4.86.

EXAMPLE 7

In this test, a number of pots were planted in the greenhouse with Kentucky-31 fescue and were grown for about 8 weeks. The compounds to be applied were formulated in acetone and water, and about 0.5 percent of a surface-active agent was added. The height of the grass in each pot was measured, and treatments at the rates indicated below were made with a hand sprayer. The pots are returned to the greenhouse and watered as before and the heights of the plants in the control and test pots are measured and recorded each week.

In the following tables, the reduction or retardation in the rate of turfgrass growth induced by the compounds of the present invention is expressed in terms of the percent reduction in the growth of treated turfgrass during the test period relative to the growth of untreated turfgrass during the test period. The percent reduction is determined in accordance with the general equation:

$$\text{Percent Reduction} = \left[1 - \frac{\text{Growth of Treated Turfgrass}}{\text{Growth of Untreated Turfgrass}}\right] \times 100$$

The growth of the treated and untreated turfgrass as used in the above equation is the difference in the height of the turfgrass before the test and the height of the treated or untreated turfgrass at the end of the test period.

Tables I–VI summarize the results of six separate tests conducted in accordance with this procedure.

TABLE I

| Compound of Example No. | Rate (kg/ha) | Percent Reduction Test Period | | | |
|---|---|---|---|---|---|
| | | 1st Week | 2nd Week | 3rd Week | 4th Week |
| 1 | 0.56 | 25 | 17 | 22 | 15 |
| | 2.24 | 35 | 43 | 55 | 73 |
| | 5.60 | 19 | 32 | 46 | 64 |
| 4 | 0.56 | 13 | 31 | 25 | 29 |
| | 2.24 | 23 | 27 | 44 | 64 |
| | 5.60 | 39 | 28 | 54 | 70 |

TABLE II

| Compound of Example No. | Rate (kg/ha) | Percent Reduction Test Period | |
|---|---|---|---|
| | | 1st Week | 2nd Week |
| 2 | 5.60 | 62 | 74 |
| 3 | 5.60 | 97 | 100 |
| 4 | 5.60 | 37 | 74 |

TABLE III

| Compound of Example No. | Rate (kg/ha) | Percent Reduction Test Period | |
|---|---|---|---|
| | | 1st Week | 2nd Week |
| 1 | 5.60 | 84 | 100 |
| 6 | 5.60 | 84 | 96 |

TABLE IV

| Compound of Example No. | Rate (kg/ha) | Percent Reduction Test Period | | |
|---|---|---|---|---|
| | | 1st Week | 2nd Week | 3rd Week |
| 1 | 0.28 | 75 | 81 | 81 |
| | 1.12 | 67 | 80 | 84 |
| | 3.36 | 76 | 80 | 86 |
| 2 | 0.28 | 61 | 81 | 84 |
| | 1.12 | 73 | 81 | 81 |
| | 3.36 | 65 | 78 | 82 |
| 3 | 0.28 | 63 | 77 | 83 |
| | 1.12 | 64 | 79 | 83 |
| | 3.36 | 75 | 80 | 83 |
| 5 | 0.28 | 58 | 43 | 29 |
| | 1.12 | 71 | 81 | 82 |
| | 3.36 | 75 | 88 | 86 |
| 6 | 0.28 | 62 | 73 | 79 |
| | 1.12 | 65 | 77 | 79 |
| | 3.36 | 75 | 81 | 87 |

TABLE V

| Compound of Example No. | Rate (kg/ha) | Percent Reduction Test Period | |
|---|---|---|---|
| | | 1st Week | 2nd Week |
| 1 | 0.28 | 42 | 80 |
| | 1.12 | 37 | 82 |
| | 3.36 | 31 | 89 |
| 4 | 5.60 | 77 | 90 |

TABLE VI

| Compound of Example No. | Rate (kg/ha) | Percent Reduction Test Period | |
|---|---|---|---|
| | | 1st Week | 2nd Week |
| 1 | 0.28 | 60 | 70 |
| | 1.12 | 75 | 81 |
| | 3.36 | 69 | 76 |
| 4 | 0.28 | 43 | 63 |
| | 1.12 | 62 | 69 |
| | 3.36 | 68 | 74 |

As illustrated by the above example, one result of applying the compounds of the present invention to turfgrass is reduced growth of treated turfgrass in particular the height of the turfgrass relative to the growth of untreated plants. Other desirable results include increased density of the turfgrass, darkening of the color of the turfgrass and no adverse effect on the root system of the turfgrass.

From the illustrative data presented in the foregoing example, it should be clear that selection of an appropriate rate of application to obtain the desired effects on grass height and seedhead suppression will be dependent upon several factors. As well understood by those skilled in the art, such factors include the variety of turfgrass, the stage of grass maturity, and the nature and location of the area to be treated. In general, it has been found that desired results can be obtained at application rates of from about 0.1 to about 10.0 pounds per acre. It has further been found to be preferred to employ the compounds of the invention at rates of from about 1.0 to about 6.0 pounds per acre.

The growth regulating compositions of this invention, including concentrates which require dilution prior to application to the plants, contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The growth regulating compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent," it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, ditertiary acetylenic glycols, polyoxyethylene derivatives of alkylphenols (particularly isooctylphenol) and nonylphenol) and polyoxyethylene derivatives of the mono-higher fatty acid esters of hexitol anhydrides (e.g. sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acid) laurates.

Water-dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible powder of this invention usually contains from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform.

Emulsifiable oils are usually solutions of active ingredient in water-immiscible or partially water-immiscible solvents together with a surface-active agent. Suitable solvents for the active ingredient of this invention include hydrocarbons and water-immiscible ethers, esters or ketones. The emulsifiable oil compositions generally contain from about 5 to 95 parts active ingredient, about 1 to 50 parts surface-active agent and about 4 to 94 parts solvent, all parts being by weight based on the total weight of emulsifiable oil.

| I. Emulsifiable Concentrates | |
|---|---|
| | Weight Percent |
| A. Compound of Example No. 4 | 50.0 |
| Calcium dodecylbenzene sulfonate/polyoxyethylene ethers blend (e.g., Atlox ® 3437F and Atlox 3438F | 5.0 |
| Monochlorobenzene | 45.0 |
| | 100.00 |
| B. Compound of Example No. 1 | 85.0 |
| Calcium dodecyl sulfonate/alkylaryl polyether alcohol blend | 4.0 |
| C9 aromatic hydrocarbons solvent | 11.0 |
| | 100.00 |
| C. Compound of Example No. 1 | 5.0 |
| Calcium dodecylbenzene sulfonate/ polyoxyethylene ethers blend (e.g., Atlox 3437F | 1.0 |
| Xylene | 94.0 |
| | 100.00 |

| II. Liquid Concentrates | | |
|---|---|---|
| A. | Compound of Example No 1. | 10.0 |
| | Xylene | 90.0 |
| | | 100.00 |
| B. | Compound of Example No. 1 | 85.0 |
| | Dimethyl sulfoxide | 15.0 |
| | | 100.00 |
| C. | Compound of Example No. 4 | 50.0 |
| | N-methylpyrrolidone | 50.0 |
| | | 100.00 |
| D. | Compound of Example No. 4 | 5.0 |
| | Ethoxylated castor oil | 20.0 |
| | Rhodamine B | .5 |
| | Dimethyl formamide | 74.5 |
| | | 100.0 |

| III. Emulsions | |
|---|---|
| | Weight Percent |
| A. Compound of Example No. 1 | 40.0 |
| Polyoxyethylene/polyoxypropylene block copolymer with butanol (e.g., Tergitol ® XH) | 4.0 |
| Water | 56.0 |
| | 100.00 |
| B. Compound of Example No. 3 | 5.0 |
| Polyoxyethylene/polyoxypropylene block copolymer with butanol | 3.5 |
| Water | 91.5 |
| | 100.00 |

| IV. Wettable Powders | | |
|---|---|---|
| | | Weight Percent |
| A. | Compound of Example No. 1 | 25.0 |
| | Sodium lignosulfonate | 3.0 |
| | Sodium N-methyl-N-oleyl-taurate | 1.0 |
| | Amorphous silica (synthetic) | 71.0 |
| | | 100.00 |
| B. | Compound of Example No. 6 | 80.0 |
| | Sodium dioctyl sulfosuccinate | 1.25 |
| | Calcium lignosulfonate | 2.75 |

-continued

IV. Wettable Powders

| | | Weight Percent |
|---|---|---|
| | Amorphous silica (synthetic) | 16.00 |
| | | 100.00 |
| C. | Compound of Example No. 4 | 10.0 |
| | Sodium lignosulfonate | 3.0 |
| | Sodium N-methyl-N-oleyl-taurate | 1.0 |
| | Kaolinite clay | 86.0 |
| | | 100.00 |

V. Dusts

| | | Weight Percent |
|---|---|---|
| A. | Compound of Example No. 4 | 2.0 |
| | Attapulgite | 98.0 |
| | | 100.00 |
| B. | Compound of Example No. 2 | 60.0 |
| | Moutmorillonite | 40.00 |
| | | 100.00 |
| C. | Compound of Example No. 5 | 30.00 |
| | Bentonite | 70.0 |
| | | 100.00 |
| D. | Compound of Example No. 1 | 1.0 |
| | Diatomaceous earth | 99.0 |
| | | 100.00 |

VI. Granules

| | | Weight Percent |
|---|---|---|
| A. | Compound of Example No. 1 | 15.0 |
| | Granular attapulgite (20/40 mesh) | 85.0 |
| | | 100.00 |
| B. | Compound of Example No. 12 | 30.0 |
| | Diatomaceous earth (20/40) | 70.0 |
| | | 100.00 |
| C. | Compound of Example No. 13 | 0.5 |
| | Bentonite (20/40) | 99.5 |
| | | 100.00 |
| D. | Compound of Example No. 14 | 5.0 |
| | Pyrophyllite (20/40) | 95.0 |
| | | 100.00 |

VII. Microcapsules

| | | Weight Percent |
|---|---|---|
| A. | Compound of Example No. 4 encapsulated in polyurea shell wall | 49.2 |
| | Sodium lignosulfonate (e.g. Reax® 88B) | 0.9 |
| | Water | 49.9 |
| | | 100.00 |
| B. | Compound of Example No. 1 encapsulated in polyurea shell wall | 10.0 |
| | Potassium lignosulfonate (e.g., Reax® C-21) | .5 |
| | Water | 89.5 |
| | | 100.00 |
| C. | Compound of Example No. 1 encapsulated in polyurea shell wall | 80.0 |
| | Magnesium salt of lignosulfate (Treax® LTM) | 2.0 |
| | Water | 18.0 |
| | | 100.00 |

Although compositions of this invention can also contain other additaments, for example, fertilizers, plant growth regulants, pesticides, and the like used as adjuvants or in combination with any of the above-described adjuvants, it is preferred to employ the compositions of this invention alone with sequential treatments with the other plant growth regulants, fertilizers and the like for maximum effect. For example, the field could be sprayed with a composition of this invention either before or after being treated with fertilizers, other plant growth regulants and the like. The compositions of this invention can also be admixed with the other materials, e.g. fertilizers, other plant growth regulants, etc., and applied in a single application.

Fertilizers useful in combination with the active ingredients include, for example, ammonium nitrate, urea, potash and superphosphate. Other useful additaments include materials in which plant organisms take root and grow such as compost, manure, humus, sand and the like.

When operating in accordance with the present invention, effective growth regulating amounts of active ingredients are applied directly or indirectly to the plants. The application of liquid and particulate solid growth regulating compositions can be carried out by conventional methods, e.g., power dusters, boom and hand sprayers and spray dusters.

The application of an effective growth regulating amount of the above-described compounds to the turfgrass is essential and critical to the practice of the present invention. The exact amount of active ingredient to be applied is dependent upon the grass variety and stage of development thereof, and the environmental conditions, as well as upon the specific alpha-chloro-N-alkoxymethyl-N-(2,6-dialkoxyphenyl)acetamide employed. It should be understood that the amount of active ingredient applied must be sufficient to regulate the growth of the treated turfgrass without producing a herbicidal or killing effect thereon. It is believed that those skilled in the art can readily determine from the teachings of this specification, including examples, the appropriate application rates.

Although the invention is described with respect to specific modifications, the details thereof are not to be construed as limitations except to the extent indicated in the following claims.

What is claimed is:

1. A method for retarding the growth of turfgrass which comprises applying to said turfgrass an effective growth retarding amount of a compound of the formula

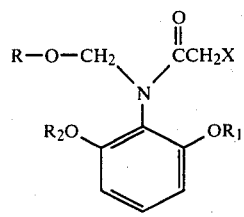

wherein R, $R_1$ and $R_2$ are independently lower alkyl and X is chloro, bromo or iodo.

2. A method according to claim 1 wherein X is chloro.

3. A method according to claim 2 wherein $R_1$ and $R_2$ are methyl.

4. A method according to claim 3 wherein the compound is alpha-chloro-N-[1-methylethoxymethyl]-N-[2,6-dimethoxyphenyl]acetamide.

5. A method according to claim 3 wherein the compound is alpha-chloro-N-(butoxymethyl)-N-(2,6-dimethoxyphenyl)acetamide.

6. A method according to claim 3 wherein the compound is alpha-chloro-N-[propoxymethyl]-N-[2,6-dimethoxyphenyl]acetamide.

7. A method according to claim 3 wherein the compound is alpha-chloro-N-[2-methylpropoxymethyl]-N-[2,6-dimethoxyphenyl]acetamide.

8. A method according to claim 3 wherein the compound is alpha-chloro-N-(methoxymethyl)-N-(2,6-dimethoxyphenyl)acetamide.

9. A method according to claim 3 wherein the compound is alpha-chloro-N-(ethoxymethyl)-N-(2,6-dimethoxyphenyl)acetamide.

* * * * *